United States Patent [19]

Cross et al.

[11] 4,339,583

[45] * Jul. 13, 1982

[54] (IMIDAZOLYLMETHYL)PYRIDINE COMPOUNDS AS THROMBOXANE SYNTHETASE INHIBITORS

[75] Inventors: Peter E. Cross, Canterbury; Roger P. Dickinson, Dover, both of England

[73] Assignee: Pfizer Inc., New York, N.Y.

[ * ] Notice: The portion of the term of this patent subsequent to Oct. 28, 1997, has been disclaimed.

[21] Appl. No.: 208,675

[22] Filed: Nov. 20, 1980

[30] Foreign Application Priority Data

Nov. 27, 1979 [GB] United Kingdom ................ 7940848

[51] Int. Cl.³ ............... C07D 401/06; C07D 401/00; C07D 413/00

[52] U.S. Cl. ............................ 546/256; 544/131; 546/276; 546/278; 424/248.51; 424/248.54; 424/263

[58] Field of Search ............... 546/256, 278, 276; 544/141, 131; 424/263

[56] References Cited

U.S. PATENT DOCUMENTS

| | | | |
|---|---|---|---|
| 3,417,091 | 12/1968 | Pickholz et al. | 546/176 |
| 4,058,614 | 11/1977 | Baldwin | 546/278 X |
| 4,177,350 | 12/1979 | Zirngibl et al. | 546/278 |
| 4,230,714 | 10/1980 | Cross et al. | 424/263 |

FOREIGN PATENT DOCUMENTS

878230 2/1980 Belgium .
3560 8/1979 European Pat. Off. .

*Primary Examiner*—Joseph Paul Brust
*Attorney, Agent, or Firm*—Connolly and Hutz

[57] ABSTRACT

Certain 2-(1-imidazolylmethyl)pyridine compounds, having a further substituent O—Y—Z at the 3- or 5-position of the pyridine ring. Y is —$(CH_2)_n$—, —$CH_2C_6H_4$—, or —$CH_2(Het)$—, where n is an integer from 1 to 4 and Het is a heterocyclic group; Z is a carboxy (COOH) or carboxycarbonyl (COCOOH) group, or an ester or amide derivative thereof. The compounds of the invention selectively inhibit the thromboxane synthetase enzyme, without significantly inhibiting the action of the prostacyclic or cyclo-oxygenase enzymes in animals, including man. The compounds are useful, therefore, in the treatment of thrombosis, ischaemic heart disease, stroke, transient ischaemic attack, migraine and the vascular complications of diabetes.

21 Claims, No Drawings

(IMIDAZOLYLMETHYL)PYRIDINE COMPOUNDS AS THROMBOXANE SYNTHETASE INHIBITORS

BACKGROUND OF THE INVENTION

This invention relates to pyridine derivatives and in particular to certain 2-(1-imidazolymethyl)pyridine derivatives substituted in the pyridine ring. Such compounds are able to selectively inhibit the action of the thromboxane synthetase enzyme without significantly inhibiting the action of the prostacyclin synthetase or cyclo-oxygenase enzymes. The compounds are useful in, for example, the treatment of thrombosis, ischaemic heart disease, stroke, transient ischaemic attack, migraine and the vascular complications of diabetes.

European patent application No. 79100289.2, published Aug. 22, 1979 under No. 3,560, and U.S. Pat. No. 4,230,714 both disclose inhibitors of thromboxane synthetase.

SUMMARY OF THE INVENTION

According to the invention there are provided compounds of the formula:

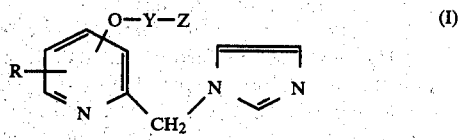

and the pharmaceutically-acceptable acid-addition salts thereof;

wherein R is hydrogen, alkyl having 1 to 4 carbon atoms or halo;

Y is

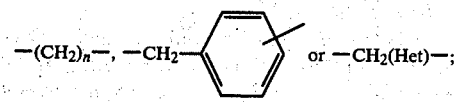

and Z is $COOR^1$, $CONHR^2$, $CONR^3R^4$, $COCOOR^1$, $COCONHR^2$, $COCONR^3R^4$, CN or 5-tetrazolyl;

wherein n is an integer from 1 to 4;

Het represents a 5- or 6-membered aromatic heterocyclic ring linked to Z by a ring carbon atom;

$R^1$ is hydrogen or alkyl having 1 to 4 carbon atoms;

$R^2$ is hydrogen, alkyl having 1 to 4 carbon atoms, alkanoyl having 2 to 4 carbon atoms, alkylsulphonyl having 1 to 4 carbon atoms, cyano, benzoyl or benzenesulphonyl, the phenyl ring in said benzoyl and benzenesulphonyl groups being optionally substituted with one or more radicals selected from alkyl having 1 to 4 carbon atoms, alkoxy having 1 to 4 carbon atoms, trifluoromethyl and halo;

and $R^3$ and $R^4$ are each alkyl having 1 to 4 carbon atoms, or $R^3$ and $R^4$ taken together with the nitrogen atom to which they are attached form a pyrrolidino, piperidino or morpholino group;

and when Y is —CH₂(Het), Z can further comprise an alkyl group having 1 to 4 carbon atoms;

provided that the O—Y—Z group is at the 3- or 5-position of the pyridine ring.

A preferred group of compounds of the invention are those in which Y is a group:

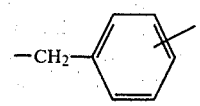

particularly where the substituent Z is in the 4-position. Also preferred are compounds where Y is a group:

particularly where Het is a 2- or 3-pyridyl or 2-thienyl group. Preferred substituents Z are $CO_2H$, $CO_2R^1$ (where $R^1$ is methyl or ethyl) and $CONH_2$.

Particularly preferred individual compounds of the invention are 3-(4-carboxybenzyloxy)-2-(1-imidazolylmethyl)pyridine and 3-(4-carbamoylbenzyloxy)-2-(1-imidazolylmethyl)pyridine.

The invention also provides a method of inhibiting the action of the thromboxane synthetase enzyme in an animal, including a human being, without significantly inhibiting the action of the prostacyclin synthetase or cyclo-oxygenase enzymes, which comprises administering to the animal an effective amount of a compound of the formula (I), or a pharmaceutically acceptable salt thereof, or a pharmaceutical composition comprising such a compound or salt together with a pharmaceutically acceptable diluent or carrier.

The invention further provides a compound of the formula (I), or a pharmaceutically acceptable salt thereof, or pharmaceutical composition comprising such a compound or salt together with a pharmaceutically acceptable diluent or carrier, for use in treating an animal, including a human being, to inhibit the action of the thromboxane synthetase enzyme without significantly inhibiting the action of the prostacyclin synthetase or cyclo-oxygenase enzymes.

The invention also includes a pharmaceutical composition comprising a compound of the formula (I), or a pharmaceutically-acceptable salt or bioprecursor thereof, together with a pharmaceutically acceptable diluent or carrier.

The invention also includes pharmaceutically acceptable bioprecursors of compounds of the formula (I). For the purpose of this specification the term "pharmaceutically acceptable bioprecursor" of a compound of the formula (I) means a compound having a structural formula different from the compounds of the formula (I) but which nonetheless, upon administration to an animal or human being, is converted in the patient's body to a compound of the formula (I).

DETAILED DESCRIPTION OF THE INVENTION

Pharmaceutically acceptable acid addition salts of the compounds of the invention are salts with acids containing pharmaceutically acceptable anions, e.g., the hydrochloride, hydrobromide, sulphate or bisulphate, phosphate or acid phosphate, acetate, maleate, fumarate, lactate, tartrate, citrate, gluconate, succinate and p-toluene sulphonate salts.

In this specification "halo" indicates fluoro, chloro, bromo or iodo. Alkyl and alkoxy groups having 3 or more carbon atoms may be straight or branched chain. Alkanoyl groups having 4 carbon atoms may be straight or branched chain.

The aromatic heterocyclic group (Het) may contain as hetero atom a single nitrogen, oxygen or sulphur atom or a nitrogen atom together with a further nitrogen, oxygen or sulphur atom. Thus, Het may be for example a pyridine, thiophene, furan, pyrazole or isoxazole ring.

The compounds of the invention may be prepared by a number of different routes. In one process according to the invention the compounds of the formula (I) may be prepared from a hydroxy-pyridine of the formula:

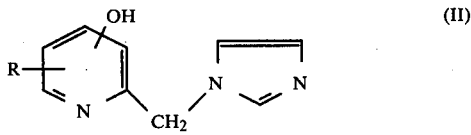
(II)

where R is as previously defined, by first reacting with an alkali metal base and then reacting with a compound of the formula:

(III)

where Y and Z are as previously defined and Hal means chloro, bromo or iodo.

A preferred alkali metal base is an alkali metal hydride and in this case the reaction is conveniently performed by adding one equivalent of the alkali metal hydride, e.g., sodium hydride, to a solution of the hydroxy-pyridine (II) in a dry, inert organic solvent, e.g., N,N-dimethylformamide or dimethylsulphoxide. The hydride is conveniently used in the form of a dispersion in a mineral oil. The reaction mixture is stirred at room temperature and the initial reaction is generally complete within one or two hours.

The reaction may also be achieved using an alkali metal hydroxide, e.g., sodium hydroxide, and in this case the hydroxy-pyridine may be stirred in an aqueous or aqueous organic solution of the hydroxide at room temperature for 10–15 minutes.

The solution is cooled and the halide (III) is added, preferably in an amount of 1 equivalent or a slight (e.g., 10%) excess. The reaction may be allowed to proceed to completion at room temperature, but it is sometimes advantageous to heat the reaction mixture, e.g., at 100° C. to accelerate the reaction. The time taken for the reaction to go substantially to completion will naturally depend on the precise conditions and temperature used and on the nature of the reactants. We have found, however, that even with the less reactive compounds a period of 5 hours at 100° C. is generally sufficient to ensure that the reaction is substantially complete. The reaction product is worked up in a conventional manner, e.g., by removal of the solvent under vacuum or by pouring the reaction mixture into water to precipitate the product. The crude product is purified by solvent extraction and washing and may be further purified, if desired, by crystallization or chromatography.

Naturally, certain of the groups Z may be obtained by chemical transformation reactions, and these possibilities will be well known to those skilled in the art. Thus, for example, the compounds of the formula (I), where Z is a carboxyl or glyoxylic acid group, may be obtained via hydrolysis of the corresponding esters where Z is a group $CO_2R^1$ or $COCO_2R^1$ and $R^1$ is a lower alkyl group. Alternatively, treatment of the esters with ammonia gives the amides where Z is $CONH_2$ or $COCONH_2$. The amides where Z is $CONH_2$ may alternatively be prepared via hydrolysis of the compound of formula (I) wherein Z is a cyano group using concentrated hydrochloric acid or, in the case of aromatic nitriles, alkaline hydrogen peroxide. Acid hydrolysis of the nitriles can also be used to yield the corresponding acids where Z is a carboxyl group. The acids may be further converted to a variety of derivatives by conventional methods, thus formation of the acid chloride, e.g., by reaction with thionylchloride followed by reaction with ammonia or a $C_1$–$C_4$ lower alkylamine gives compounds where Z is $CONHR^2$ or $COCONHR^2$ and $R^2$ is hydrogen or lower alkyl respectively, or alternatively, reaction of the acid chloride with a di-lower alkylamine or with pyrrolidine, piperidine, or morpholine gives compounds where Z is $CONR^3R^4$ or $COCONR^3R^4$.

Alternatively, the acid may be reacted with N,N'-carbonyldiimidazole and the adduct reacted with a lower alkylamine or amide to give N-substituted amido products. The compounds where $R^2$ is an alkylsulphonyl, benzenesulphonyl or cyano group may similarly be prepared by reacting the corresponding acid where Z is $CO_2H$ or $COCO_2H$ with N,N'-carbonyldiimidazole and adding the required alkylsulphonamide, benzene sulphonamide or cyanamide respectively; the product in these cases often being isolated in its tautomeric form, i.e., as a carboximidic acid derivative.

The unsubstituted amides where Z is $CONH_2$ or $COCONH_2$ may also be further reacted, thus acylation using the imidazolide prepared from a $C_2$–$C_4$ alkanoic acid or benzoic acid gives the corresponding substituted derivative where $R^2$ is a $C_2$–$C_4$ alkanoyl or a benzoyl group respectively.

Compounds where Z is 5-tetrazolyl are prepared from the corresponding cyano derivative by reaction with sodium azide and ammonium chloride.

All the above transformation reactions are quite conventional and conditions required for their performance will be well known to those skilled in the art as will other possibilities and variations.

The starting materials of formula (II) and methods for their preparation are described in pending British Patent Application No. 79.26146, which was published on Mar. 5, 1980, under No. 2,028,317A.

The compounds of formula (I) have been found to selectively inhibit the action of the thromboxane synthetase enzyme without significantly affecting the action of the prostacyclin synthetase or cyclo-oxygenase enzymes. Thus the compounds are of value in the treatment of a variety of clinical conditions which are characterized by an imbalance of prostacyclin/thromboxane $A_2$. For the reasons given below, these conditions may include thrombosis, ischaemic heart disease, stroke, transient ischaemic attack, migraine and the vascular complications of diabetes.

Research work has established that in most tissues the major product of the arachidonic acid metabolism is either of two unstable substances, thromboxane $A_2$ ($TxA_2$) or prostacyclin ($PGI_2$). (Proc. Nat. Acad. Sci. U.S.A., 1975, 72, 2994, Nature, 1976, 263, 663, Prostaglandins, 1976, 12, 897). In most cases the prostaglandins $PGE_2$, $PGF_2$ and $PGD_2$ are comparatively minor by-products in this bio-synthetic pathway. The discovery of thromboxane $A_2$ and prostacyclin has significantly increased our understanding of vascular homeostasis; prostacyclin, for instance, is a powerful vasodilator and inhibitor of platelet aggregation, and in this last respect is the most potent endogenous substance so far discovered. The prostacyclin synthetase enzyme is located in the endothelial layer of the vasculature, and is fed by endoperoxides released by blood platelets coming into contact with the vessel wall. The prostacyclin thus produced is important for prevention of platelet deposition on vessel walls. (Prostaglandins, 1976, 12, 685, Science, 1976, 17, Nature, 1978, 273, 765).

Thromboxane $A_2$ is synthesized by the thromboxane synthetase enzyme which is located in, for example, the blood platlets. Thromboxane $A_2$ is a powerful vasoconstrictor and pro-aggregatory substance. As such, its actions are in direct opposition to those of prostacyclin. If, for any reason, prostacyclin formation by the vasculature is impaired, then the endoperoxides produced by platelets coming into contact with the vessel wall are converted into thromboxane, but are not converted effectively into prostacyclin (Lancet, 1977, 18, Prostaglandins, 1978, 13, 3). Alteration of the prostacyclin/thromboxane balance in favor of the latter substance could result in platelet aggregation, vasospasm (Lancet, 1977, 479, Science, 1976, 1135, Amer. J. Cardiology, 1978, 41, 787) and an increased susceptibility to atherothrombosis (Lancet (i) 1977, 1216). It is also known that in experimental atherosclerosis prostacyclin generation is suppressed and thromboxane $A_2$ production is enhanced (Prostaglandins, 1977, 14, 1025 and 1035). Thus thromboxane $A_2$ has been implicated as the causative agent in variant angina, myocardial infarction, sudden cardiac death and stroke (Thromb. Haemostasis, 1977, 38, 132). Studies in rabbits have shown that ECG changes typical of these conditions were produced when freshly prepared thromboxane $A_2$ was injected directly into the animal's heart (Biochem. aspects of Prostaglandins and Thromboxanes, Editors, N. Kharasch and J. Fried, Academic Press 1977 page 189). This technique is considered to represent a unique animal model of the heart attacks of coronary patients and has been used to show that administration of a compound believed to antagonize the effects of thromboxane $A_2$ protects the rabbits from the adverse consequences of thromboxane $A_2$ injection.

Another area where a $PGI_2/TxA_2$ imbalance is considered to be a contributory factor is that of migraine. The migraine headache is associated with changes in intra and extra-cerebral blood flow, in particular, a pre-headache reduction of cerebral blood flow followed by dilatation in both vascular areas during the headache phase.

Prior to the development of the headache, blood levels of 5-hydroxytryptamine are elevated, and this suggests the occurrence of in vivo aggregation and release of the amine from the platelet stores. It is known that the blood platelets of migraine patients are more prone to aggregate than are those of normal individuals (J. Clin. Pathol., 1971, 24, 250, J. Headache, 1977, 17, 101). Furthermore, it has now been postulated that not only is an abnormality of platelet function a major factor in the pathogenesis of migraine attacks, but it is in fact their prime cause (Lancet (i), 1978, 501). Thus a drug that selectively modifies platelet function to inhibit thromboxane $A_2$ formation could be of considerable benefit in migraine therapy.

Abnormalities of platelet behavior have been reported in patients with diabetes mellitus (Metabolism, 1979, 28, 394, Lancet, 1978 (i) 235). Diabetic patients are known to be particularly susceptible to microvascular complications, atherosclerosis and thrombosis, and platelet hyper-reactivity has been suggested as the cause of such angiopathy. Diabetic platelets produce elevated amounts of $TxB_2$ and malondialdehyde (Symposium "Diabetes and Thrombosis—Implications for Therapy", Leeds U.K., April 1979). Also it has been shown that in rats with experimental diabetes vascular prostacyclin production is impaired and $TxA_2$ synthesis from the platelets is elevated (IV International Prostaglandin Conference, Washington, D.C. May 1979). Thus the imbalance between prostacyclin and $TxA_2$ is considered to be responsible for the microvascular complications of diabetes. A $TxA_2$-synthetase inhibitor could, therefore, find clinical utility in preventing these vascular complications.

Aspirin and most other non-steroidal anti-inflammatory drugs inhibit the cyclo-oxygenase enzyme. The effect of this is to shut down the production of the $PGG_2/H_2$ endoperoxides and by so doing to reduce both the prostacyclin and thromboxane $A_2$ levels. Aspirin and aspirin-like drugs have been evaluated clinically for prevention of stroke and heart attack (New England and J. Med. 1978, 299, 53, B.M.J., 1978, 1188, Stroke, 1977, 8, 301).

Although some encouraging results have been obtained with these drugs, a compound which specifically inhibits thromboxane $A_2$ formation leaving the biosynthesis of prostacyclin unimpaired would be more valuable in these clinical conditions (Lancet (ii), 1978, 780).

The effect of the compounds of the formula (I) on the thromboxane synthetase enzyme, and the prostacyclin synthetase and cyclo-oxygenase enzymes has been measured by the following in vitro enzyme assays:

1. Cyclo-oxygenase

Ram seminal vesicle microsomes (Biochemistry, 1971, 10, 2372) are incubated with arachidonic acid (100 $\mu M$: 1 min.: 22°) to produce $PGH_2$ and aliquots of the reaction mixture injected into a stream of Krebs-bicarbonate at 37° C. (containing a mixture of antagonists (Nature, 1978, 218, 1135) and indomethacin (Brit. J. Pharmacol., 1972, 45 451) which is superfusing a spirally-cut rabbit aorta strip (Nature, 1969, 223, 29). The ability of a compound to inhibit the enzyme is measured by comparing the increases in isometric tension produced by $PGH_2$ in the absence of the test compound, and following preincubation of the enzyme with the test compound for 5 minutes.

2. Prostacyclin ($PGI_2$) Synthetase

Pig aorta microsomes (Nature, 1976, 263, 663) are incubated (30 sec.: 22° C.) with $PGH_2$ produced as in 1) and aliquots bio-assayed as in 1. $PGI_2$ production is assessed indirectly by measuring the decrease in $PGH_2$-induced tension ($PGI_2$ itself does not contract the aorta). This decrease can be prevented completely by pre-incubation of the enzyme with the selective $PGI_2$ synthetase inhibitor, 15-hydroxy-arachidonic acid (Prostaglandins, 1976, 12, 715). The test compound is then pre-incubated with the enzyme for 5 minutes, and its ability to prevent the decrease in tension is measured.

3. Thromboxane $A_2$ ($TxA_2$) Synthetase

Indomethacin pre-treated human platelet microsomes (Science, 1976, 193, 163) are incubated (2 min.: 0° C.) with $PGH_2$ produced as in 1) and aliquots of the reaction mixture superfused over two rabbit aorta spirals which are separated by a delay coil (2 min.). The latter is required to allow the selective decay of the more unstable thromboxane $A_2$ (Proc. Nat. Acad. Sci., 1975, 72, 2994) thereby enabling the separate measurement of increased isometric tension due to the $TxA_2$ formed and the $PGH_2$ remaining. The test compound is pre-incubated with enzyme for 5 minutes, and its ability to inhibit the thromboxane synthetase enzyme is measured as its reduction of the $TxA_2$ component of the isometric tension.

Compounds of the invention tested in this way have been shown to be capable of selectively inhibiting the thromboxane synthetase enzyme.

In addition to the above, an in vitro assay for measuring the inhibition of human blood platelet aggregation has been described and this may be predictive of anti-thrombotic efficacy clinically (Lancet (ii), 1974, 1223, J. Exp. Med., 1967, 126, 171). Both clinically effective agents, aspirin and sulphinpyrazone, show inhibitory activity in vitro against a variety of aggregating agents in this test.

A number of in vivo tests in animals have also been described for evaluating potential anti-thrombotic drugs. Intravenous injection of arachidonic acid causes death in rabbits by causing platelet clumping and embolization in the lungs. Again, both the clinically effective aspirin (Agents and Actions, 1977, 1, 481) and sulphinpyrazone (Pharmacology, 1976, 14, 522) protect the rabbit from the lethal effect of the injection. Sulphinpyrazone has also been shown to prevent the aggregation of platlets in an extra corporeal loop of the abdominal aorta of rats in vivo (Thromb. Diathes. Haem., 1973, 30, 138).

The compounds of formula I may be administered orally in the form of tablets or capsules containing a unit dose of the compound together with such excipients as maize starch, calcium carbonate, dicalcium phosphate, alginic acid, lactose, magnesium stearate, "Primogel TM " or talc, according to standard pharmaceutical practice. The tablets are typically prepared by granulating the ingredients together and compressing the resulting mixture to give tablets of the desired size. Capsules are typically prepared by granulating the ingredients together and filling them into hard gelatine capsules of the appropriate size to contain the desired dosage.

The compounds of formula I may also be administered parenterally, for example, by intramuscular, intravenous or subcutaneous injection, according to standard pharmaceutical practice. For parenteral administration, they are best used in the form of a sterile aqueous solution which may contain other solutes such as tonic and pH adjusters. The compounds may be added to distilled water and the pH adjusted to 3-6 using an acid such as citric, lactic or hydrochloric acid. Sufficient solutes such as dextrose or saline may be added to render the solution isotonic. The resulting solution may then be sterilized and filled into sterile glass vials of an appropriate size to contain the desired volume of solution. The compounds of the invention may also be administered by the infusion of a parenteral formulation, as described above, into a vein.

For oral administration to human patients, it is expected that the daily dosage level of a compound of formula I will be from 0.1 to 20 mg/kg per day for a typical adult patient (70 kg). For parenteral administration, it is expected that the daily dosage level of a compound of the formula (I) will be from 0.01 to 0.5 mg/kg per day, for a typical adult patient. Thus tablets or capsules can generally be expected to contain from 5 to 150 mg of the active compound for administration orally up to 3 times a day. Dosage units for parenteral administration can be expected to contain from 0.5 to 35 mg of the active compound. A typical vial could be a 10 ml vial containing 5 mg of the active compound in 6-10 ml of solution.

It should, of course, be appreciated that in any event, the physician will determine the actual dosage which will be most suitable for the individual and it will vary with the age, weight and response of the patient. The above dosages are exemplary of the average patient; there may, of course, be individual cases where higher or lower dosage ranges are merited.

The following Examples are provided solely for the purpose of further illustration.

EXAMPLE 1

3-(4-Ethoxycarbonylbenzyloxy)-2-(1-imidazolymethyl)pyridine

Sodium hydride (1.81 g of 50% dispersion in mineral oil) was added in portions to a stirred solution of 3-hydroxy-2-(1-imidazolylmethyl)pyridine (6.00 g) in dry N,N-dimethylformamide (100 ml) at 0° C. The mixture was stirred for 15 minutes and a solution of ethyl 4-bromomethyl-benzoate (8.34 g) in dry N,N-dimethylformamide (20 ml) was then added over a period of 10 minutes. The mixture was allowed to warm to room temperature, stirred for 4 hours and water (5 ml) was then added. The solution was evaporated and the residue chromatographed on silica gel, eluting with chloroform. The product-containing fractions were combined and evaporated to give an oil which solidified on trituration with diethyl ether. Recrystallization from diethyl ether gave 3-(4-ethoxycarbonylbenzyloxy)-2-(1-imidazolylmethyl)pyridine (4.85 g), m.p. 100°-101° C.

Found: C, 67.34; H, 5.76; N, 12.27. $C_{19}H_{19}N_3O_3$ requires: C, 67.64; H, 5.68; N, 12.46%.

EXAMPLE 2

3-(4-Cyanobenzyloxy)-2-(1-imidazolymethyl)pyridine

A solution of 3-hydroxy-2-(1-imidazolylmethyl)-pyridine (6.0 g) in dry N,N-dimethylformamide (100 ml) was cooled to 5° C. and stirred under nitrogen. Sodium hydride (1.8 g as a dispersion in mineral oil) was added and the mixture was stirred for 1 hour at room temperature and then cooled to 0° C. A solution of 4-cyano-benzylbromide (6.8 g) in dry N,N-dimethylformamide (25 ml) was added and the mixture stirred at room temperature for a further 3 hours and allowed to stand overnight. Water (250 ml) was added and the aqueous solution extracted with ethyl acetate (4×100 ml). The organic extracts were combined, washed with water, dried over $MgSO_4$ and evaporated to yield a solid. Recrystallization from ethyl acetate gave 3-(4-cyanobenzyloxy)-2-(1-imidazolylmethyl)pyridine (12.0 g), m.p. 159° C.

Found: C, 70.36; H, 4.76; N, 19.10. $C_{17}H_{14}N_4O$ requires: C, 70.33; H, 4.80; N, 19.30%.

EXAMPLES 3-7

The following compounds were prepared by the general method of Examples 1 or 2 using the appropriate halide:

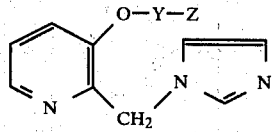

| Example | —Y—Z | M.P. (°C.) | Analysis % (Theoretical in Parenthesis) | | |
|---|---|---|---|---|---|
| | | | C | H | N |
| 3 | —CH₂CO₂C₂H₅ | 90° | 59.42 (59.76 | 5.76 5.76 | 16.02 16.08) |
| 4 | —CH₂—⟨pyridyl-N=⟩—CO₂C₂H₅ | 141–143° | 63.55 (63.89 | 5.36 5.36 | 16.69 16.56) |
| 5 | —CH₂—⟨pyridyl=N⟩—CO₂C₂H₅ | 127–128° | 61.32 (61.25 | 4.99 5.14 | 16.74 16.80) |
| 6 | —CH₂—⟨S⟩—CO₂C₂H₅ | 128° | 59.16 (59.46 | 4.96 4.99 | 12.26 12.24) |
| 7 | —CH₂—⟨pyrazolyl-CH₃, N, N-H⟩ | 138–139° | 62.44 (62.29 | 5.61 5.59 | 26.01 26.16) |

EXAMPLE 8

2-(1-Imidazolylmethyl)-3-pyridyloxy Acetic Acid Dihydrochloride

3-Hydroxy-2-(1-imidazolylmethyl)pyridine (1.0 g) was added to a stirred solution of sodium hydroxide (0.55 g) in water (5 ml) and the mixture was stirred at room temperature for 15 minutes. Chloro-acetic acid (0.65 g) was added and the mixture was warmed on an oil bath at 90° C. for 2.5 hours and then allowed to stand overnight at room temperature. The mixture was acidified with 5 N hydrochloric acid and the aqueous solution filtered and evaporated to dryness. The residue was taken up in isopropanol, the solution filtered and the filtrate concentrated and cooled. The resulting precipitate of the product was collected by filtration and recrystallized from a mixture of isopropanol and water to give 2-(1-imidazolylmethyl-3-pyridyloxy acetic acid dihydrochloride (230 mg), m.p. 235° C. Found: C, 43.07; H, 4.36; N, 13.21. C₁₁H₁₁N₃O₃.2HCl requires: C, 43.15; H, 4.28; N, 13.72%.

EXAMPLE 9

Ethyl 4-[2-(1-Imidazolylmethyl)-3-pyridyloxymethyl]-phenyl-glyoxylate

3-Hydroxy-2-(1-imidazolylmethyl)pyridine (2.63 g) was added to a solution of sodium hydroxide (0.6 g) in water (2 ml) and N,N-dimethylformamide (100 ml). The solution was stirred and ethyl 4-bromomethylphenyl glyoxylate (4.07 g) added dropwise. The mixture was heated at 55° C. for 4.5 hours and then evaporated to dryness. Water (100 ml) was added to the residue and the mixture extracted with chloroform (3×50 ml). The combined extracts were washed with water, dried and evaporated to yield an oil which was solidified by trituration with diethyl ether and collected by filtration to give ethyl 4-[2-(1-imidazolylmethyl)-3-pyridyloxymethyl]-phenyl glyoxylate (3.4 g), m.p. 115° C. (from toluene/petroleum ether). Found: C, 65.79; H, 5.23; N, 11.45. C₂₀H₁₉N₃O₄ requires: C, 65.74; H, 5.24; N, 11.50%.

EXAMPLE 10

4-[2-(1-Imidazolylmethyl)-3-pyridyloxymethyl]-phenyl-glyoxylic Acid

The ester of Example 9 (1.1 g) was added to a solution of sodium (0.07 g) in ethanol (2 ml) and the mixture stirred for 1 hour before the addition of water (1.0 ml). The mixture was stirred overnight at room temperature and water (75 ml) then added and the mixture extracted several times with chloroform. The combined organic extracts were dried and evaporated and the solid residue recrystallized from ethanol to yield 4-[2-(1-imidazolylmethyl)-3-pyridyloxymethyl]-phenyl-glyoxylic acid (0.42 g), m.p. over 250° C. Found: C, 62.67; H, 4.34; N, 11.80. C₁₈N₁₅N₃O₄.½H₂O requires: C, 62.42; H, 4.66; N, 12.13%.

EXAMPLE 11

3-(4-Carboxybenzyloxy)-2-(1-imidazolylmethyl)pyridine 3-(4-Ethoxycarbonylbenzyloxy)-2-(1-imidazolylmethyl)pyridine (4.50 g) was heated in a solution of sodium hydroxide (0.70 g) in water (125 ml) for 100° C. for 2 hours. The solution was cooled and neutralized by the addition of 2 N hydrochloric acid. The solid product was collected by filtration and recrystallized from ethanol to give 3-(4-carboxybenzyloxy)-2-(1-imidazolylmethyl)pyridine (2.80 g), m.p. 210°–211° C. Found: C, 66.06; H, 4.74; N, 13.42. C₁₇H₁₅N₃O₃ requires: C, 66.01; H, 4.89; N, 13.59%.

EXAMPLE 12

3-(4-Carbamoylbenzyloxy)-2-(1-imidazolylmethyl)pyridine

A mixture of 3-(4-carboxybenzyloxy)-2-(1-imidazolylmethyl)pyridine (1.50 g) and thionyl chloride (20 ml) was heated under reflux for 1 hour. The thionyl chloride was evaporated under reduced pressure and the residue was added to concentrated aqueous ammonia (50 ml, S.G. 0.880). The mixture was stirred for 1 hour at room temperature and the solid product was collected by filtration, washed with water, dried and crystallized from a mixture of isopropanol and petroleum ether to give 3-(4-carbamoylbenzyloxy)-2-(1-imidazolylmethyl)pyridine (1.00 g) m.p. 211°–212° C. Found: C, 66.22; H, 5.23; N, 18.17. C₁₇H₁₆N₄O₂ requires: C, 65.85; H, 5.11; N, 18.07%.

EXAMPLE 13

2-(1-Imidazolylmethyl)-3-pyridyloxy Acetamide

Ethyl 2-(1-imidazolylmethyl)-3-pyridyloxy acetate (1.8 g) was dissolved in ethanol (10 ml) and concentrated aqueous ammonia (30 ml, S.G. 0.880) was added with stirring. After two hours the solution was evaporated to dryness under vacuum and the residue triturated with dry diethyl ether. The product was collected by filtration and recrystallized from a mixture of isopropanol and ethyl acetate to yield 2-(1-imidazolylmethyl)-3-pyridyloxy acetamide (0.34 g), m.p. 159° C. Found: C, 57.11; H, 5.23; N, 23.95. C₁₁H₁₂N₄O₂ requires: C, 56.89; H, 5.21; N, 24.13%.

EXAMPLES 14-17

The following compounds were prepared by the general method of Example 13 starting with the appropriate ester.

TABLE

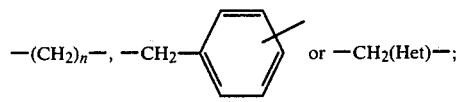

| Example | —Y—Z | M.P. (°C.) | Analysis % (Theoretical in Parenthesis) | | |
|---|---|---|---|---|---|
| | | | C | H | N |
| 14 | —CH₂—⟨phenyl⟩—COCONH₂ | 178–179° | 63.9 (64.3 | 4.8 4.8 | 16.5 16.7) |
| 15 | —CH₂—⟨pyridyl-N⟩—CONH₂ | 220° | 62.10 (62.12 | 5.02 4.89 | 22.57 22.64) |
| 16 | —CH₂—⟨pyridyl-N⟩—CONH₂ | 180° | 61.87 (62.12 | 4.89 4.89 | 22.77 22.64) |
| 17 | —CH₂—⟨S-thienyl⟩—CONH₂ | 189–191° | 56.96 (57.3 | 4.55 4.49 | 17.78 18.82) |

EXAMPLE 18

2-(1-Imidazolylmethyl)-3-[4-(N-phenylsulphonylcarbamoyl)benzyloxy]pyridine

Phenyl sulphonyl isocyanate (1.2 g) was added to a suspension of 3-(4-carboxybenzyloxy) 2-(1-imidazolylmethyl)pyridine (1.0 g) in dry tetrahydrofuran (40 ml) containing triethylamine (0.33 g). The mixture was stirred at room temperature for 8 hours and allowed to stand at room temperature for a further 36 hours. The solvents were evaporated under vacuum and aqueous 5% sodium bicarbonate solution (100 ml) added to the residue. The mixture was extracted with dichloromethane (3×50 ml) and the combined organic extracts dried, filtered and evaporated to yield an oil which solidified on trituration with diethyl ether. Recrystallization from aqueous methanol gave 2-(1-imidazolylmethyl)-3-[4-(N-phenylsulphonylcarbamoyl)benzyloxy]pyridine (0.38 g), m.p. above 250° C. Found: C, 61.47; H, 4.40; N, 12.63. $C_{23}H_{20}N_4O_4S$ requires: C, 61.59; H, 4.50; N, 12.49%.

We claim:

1. A compound of the formula

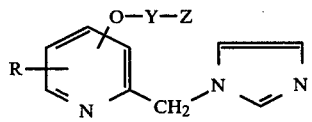

and the pharmaceutically-acceptable acid-addition salts thereof;

wherein R is hydrogen, alkyl having 1 to 4 carbon atoms or halo;

Y is $$-(CH_2)_n-, \quad -CH_2-\text{⟨phenyl⟩}- \quad \text{or} \quad -CH_2(Het)-;$$

and Z is $COOR^1$, $CONHR^2$, $CONR^3R^4$, $COCOOR^1$, $COCONHR^2$, $COCONR^3R^4$, CN or 5-tetrazolyl;

wherein n is an integer from 1 to 4;

Het represents a 2 or 3-pyridyl or 2-thienyl group linked to Z by a ring carbon atom;

$R^1$ is hydrogen or alkyl having 1 to 4 carbon atoms;

$R^2$ is hydrogen, alkyl having 1 to 4 carbon atoms, alkanoyl having 2 to 4 carbon atoms, alkylsulphonyl having 1 to 4 carbon atoms, cyano, benzoyl or benzenesulphonyl, the phenyl ring in said benzoyl and benzenesulphonyl groups being optionally substituted with one or more radicals selected from alkyl having 1 to 4 carbon atoms, alkoxy having 1 to 4 carbon atoms, trifluoromethyl and halo;

and $R^3$ and $R^4$ are each alkyl having 1 to 4 carbon atoms, or $R^3$ and $R^4$ taken together with the nitrogen atom to which they are attached form a pyrrolidino, piperidino or morpholino group;

and when Y is —CH₂(Het), Z can further comprise an alkyl group having 1 to 4 carbon atoms;

provided that the O—Y—Z group is at the 3- or 5-position of the pyridine ring.

2. A compound according to claim 1, wherein
R is hydrogen;
Y is $-(CH_2)_n-$;
and Z is $COOR^1$, $CONHR^2$, $CONR^3R^4$, $COCOOR^1$, $COCONHR^2$ or $COCONR^3R^4$, wherein $R^2$ is hydrogen or alkyl having 1 to 4 carbon atoms.

3. A compound according to claim 2, wherein n is 1.

4. A compound according to claim 3, wherein $R^3$ and $R^4$ are each alkyl having 1 to 4 carbon atoms.

5. A compound according to claim 4 wherein the O—Y—Z group is at the 3-position of the pyridine ring.

6. A compound according to claim 5, wherein Z is COOH, COOCH₂CH₃, CONH₂, COCOOH or COCOOCH₂CH₃.

7. A compound according to claim 1, wherein Y is

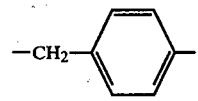

8. A compound according to claim 7, wherein Z is COOH, COOCH₃, COOCH₂CH₃ or CONH₂.

9. The compound according to claim 8, wherein R is hydrogen, Z is COOH, and the O—Y—Z group is at the 3-position on the pyridine ring.

10. The compound according to claim 8, wherein R is hydrogen, Z is CONH₂, and the O—Y—Z group is at the 3-position on the pyridine ring.

11. A compound according to claim 1, wherein
R is hydrogen;
Y is

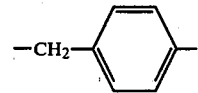

and Z is COOR$^1$, CONHR$^2$, CONR$^3$R$^4$, COCOOR$^1$, COCONHR$^2$ or COCONR$^3$R$^4$, wherein R$^2$ is hydrogen, alkyl having 1 to 4 carbon atoms or benzenesulphonyl.

12. A compound according to claim 11, wherein R$^3$ and R$^4$ are each alkyl having 1 to 4 carbon atoms.

13. A compound according to claim 12, wherein the O—Y—Z group is at the 3-position of the pyridine ring.

14. A compound according to claim 13, wherein Z is COOH, COOCH$_2$CH$_3$, CONH$_2$, COCONH$_2$, CN or CONHSO$_2$C$_6$H$_5$.

15. A compound according to claim 1, wherein Y is —CH$_2$(Het)— and Het is 2-pyridyl, 3-pyridyl or 2-thienyl.

16. A compound according to claim 15, wherein Z is COOH, COOCH$_3$, COOCH$_2$CH$_3$ or CONH$_2$.

17. A compound according to claim 1, wherein
R is hydrogen;
Y is —CH$_2$(Het)—;
and Z is COOR$^1$, CONHR$^2$, CONR$^3$R$^4$ or alkyl having 1 to 4 carbon atoms.

18. A compound according to claim 17, wherein R$^3$ and R$^4$ are each alkyl having 1 to 4 carbon atoms.

19. A compound according to claim 18, wherein the O—Y—Z group is at the 3-position of the pyridine ring.

20. A compound according to claim 19, wherein Z is COOCH$_2$CH$_3$, CONH$_2$ or CH$_3$.

21. The compound according to claim 14, wherein Z is 4-COOH.

* * * * *